US009006436B2

(12) United States Patent
Lim et al.

(10) Patent No.: US 9,006,436 B2
(45) Date of Patent: Apr. 14, 2015

(54) PREPARATION METHOD OF INTERMEDIATE OF SITAGLIPTIN

(75) Inventors: Geun Gho Lim, Seoul (KR); Sun Ki Chang, Gyeonggi-do (KR); Chang Ho Byeon, Gyeonggi-do (KR)

(73) Assignee: ST Pharm Co., Ltd., Siheung-si (KR)

( * ) Notice: Subject to any disclaimer, the term of this patent is extended or adjusted under 35 U.S.C. 154(b) by 39 days.

(21) Appl. No.: 13/977,919

(22) PCT Filed: Jan. 18, 2012

(86) PCT No.: PCT/KR2012/000408
§ 371 (c)(1),
(2), (4) Date: Sep. 12, 2013

(87) PCT Pub. No.: WO2012/099381
PCT Pub. Date: Jul. 26, 2012

(65) Prior Publication Data
US 2014/0005394 A1    Jan. 2, 2014

(30) Foreign Application Priority Data
Jan. 20, 2011    (KR) ................ 10-2011-0006081

(51) Int. Cl.
C07D 471/00    (2006.01)
C07D 487/00    (2006.01)
C07D 491/00    (2006.01)
C07D 495/00    (2006.01)
C07D 497/00    (2006.01)
C07D 487/04    (2006.01)

(52) U.S. Cl.
CPC .................... C07D 487/04 (2013.01)

(58) Field of Classification Search
None
See application file for complete search history.

(56) References Cited

U.S. PATENT DOCUMENTS

| | | | |
|---|---|---|---|
| 6,699,871 B2 | 3/2004 | Edmondson et al. | 514/249 |
| 8,030,315 B2 | 10/2011 | Kim et al. | 514/255.01 |
| 2009/0192326 A1 | 7/2009 | Perlman et al. | 560/37 |
| 2010/0317856 A1 | 12/2010 | Arjunan | 544/350 |
| 2011/0112103 A1 | 5/2011 | Kuribayashi et al. | 514/249 |
| 2012/0016125 A1 | 1/2012 | Kwak et al. | 558/303 |

FOREIGN PATENT DOCUMENTS

| | | |
|---|---|---|
| CN | 101070291 A | 11/2007 |
| JP | A 2001-300322 | 10/2001 |
| JP | A 2002-053562 | 2/2002 |
| JP | A 2008-214473 | 9/2008 |
| JP | A 2009-062290 | 3/2009 |
| JP | A 2010-202757 | 9/2010 |
| WO | WO 2009/131127 | 10/2009 |
| WO | WO 2009/131129 | 10/2009 |

OTHER PUBLICATIONS

Letter/Written Disclosure of the Information Disclosure Statement for the above-referenced application, mailed on Oct. 10, 2013, 2 pages.
ST Pharm. Website Product-Generic Intermediates, "*Arabidopsis halleri* subsp. halleri clone 99.4.1 ribosomal RNA intergenic region and external transcribed spacer region, completesequence," [online][retrieved on Aug. 12, 2013] Retrieved from:<URL:stpharm.co.kr/english/html/product/product12.asp>, 2 pages.
International Search Report, issued Oct. 4, 2012, in connection with International Patent Application No. PCT/KR2012/000408, 3 pages.
International Preliminary Report on Patentability, issued May 29, 2013, in connection with International Patent Application No. PCT/KR2012/000408, 3 pages.
Letter/Written Disclosure of the Information Disclosure Statement for the above-referenced application, mailed on Dec. 30, 2014, 2 pages.
English language abstract of International PCT Patent Publication No. WO 2009/131127, 1 page.
English language abstract of Japanese Patent Publication No. JP A 2001-300322, 1 page.
English language abstract of Japanese Patent Publication No. JP A 2002-053562, 1 page.
English language abstract of Japanese Patent Publication No. JP A 2008-214473, 1 page.
English language abstract of Japanese Patent Publication No. JP A 2009-062290, 1 page.
English language abstract of Japanese Patent Publication No. JP A 2010-202575, 1 page.
Kaminski et al., "A Study on the Activation of Carboxylic Acids by Means of 2-Chloro-4,6-dimethoxy-1,3,5-triazine and 2-Chloro-4,6-diphenoxy-1,3,5-triazine" J. Org. Chem. 63(13):4248-4255 (1998).
Kim et al., "(2R)-4-Oxo-4-[3-(Trifluoromethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV Inhibitor for the Treatment of Type 2 Diabetes" J. Med. Chem. 48(1):141-151 (2005).
Machine-generated English Language translation of Japanese Patent Publication No. JP A 2001-300322, Japan Patent Office, 9 pages.
Machine-generated English Language translation of Japanese Patent Publication No. JP A 2002-053562, Japan Patent Office, 10 pages.
Machine-generated English Language translation of Japanese Patent Publication No. JP A 2008-214473, Japan Patent Office, 16 pages.
Partial English Language translation of relevant portions of International PCT Publication No. WO 2009/131127, 2 pages.
Partial English Language translation of relevant portions of Japanese Patent Publication No. JP A 2009-062290, 2 pages.
Partial English Language translation of relevant portions of Japanese Patent Publication No. JP A 2010-202575, 2 pages.
Extended European Search Report, issued Jul. 3, 2014, in connection with corresponding European Patent Application No. 12737171.4, 3 pages.
Office Action, issued Aug. 11, 2014, and translation, in connection with corresponding Chinese Patent Application No. 201280006060.3, 10 pages.
Office Action, issued Aug. 19, 2014, and translation, in connection with corresponding Japanese Patent Application No. 550394/2013, 5 pages.

*Primary Examiner* — Jeffrey H Murray
(74) *Attorney, Agent, or Firm* — McKenna Long & Aldridge LLP; Stephanie Seidman; Frank J. Miskiel

(57) ABSTRACT

The present invention provides a method which enables the simple, economical and high-yield production which is a key intermediate of antidiabetic drug Januvia.

18 Claims, No Drawings

PREPARATION METHOD OF INTERMEDIATE OF SITAGLIPTIN

RELATED APPLICATIONS

This application is the National Stage of International Application No. PCT/KR2012/000408, filed 18 Jan. 2012, which claims benefit of priority to Korean Patent Application No. 10-2011-0006081, filed 20 Jan. 2011, the specification of which is incorporated by reference herein.

TECHNICAL FIELD

The present invention relates to a method for preparing an intermediate of sitagliptin which is an antidiabetic drug.

BACKGROUND ART

Sitagliptin is a triazolopiperazine compound having a beta-amino acid structure and has the chemical name of (2R)-4-oxo-4-[3-(trifluoromethyl)-5,6-dihydro-[1,2,4]triazolo[4,3-α]pyrazin-7(8H)-yl]-1-(2,4,5-trifluorophenyl)butan-2-amine. Sitagliptin was developed by US company, Merck & Co., Inc. Sitagliptin is the first DPP-IV inhibitor to treat type 2 diabetes and is currently commercially available in countries around the world as an antidiabetic drug under the brand name Januvia in the form of a sitagliptin phosphate monohydrate.

The intermediate of sitagliptin "t-butyl (R)-4-(3-(trifluoromethyl)-5,6-dihydro-[1,2,4]triazolo[4,3-α]pyrazin-7(8H)-yl)-1-(2,4, 5-trifluorophenyl)-4-oxobutan-2-ylcarbamate" (Compound 2 in Reaction Scheme 1 below) is prepared as in Reaction Scheme 1 and is disclosed in U.S. Pat. No. 6,699,871.

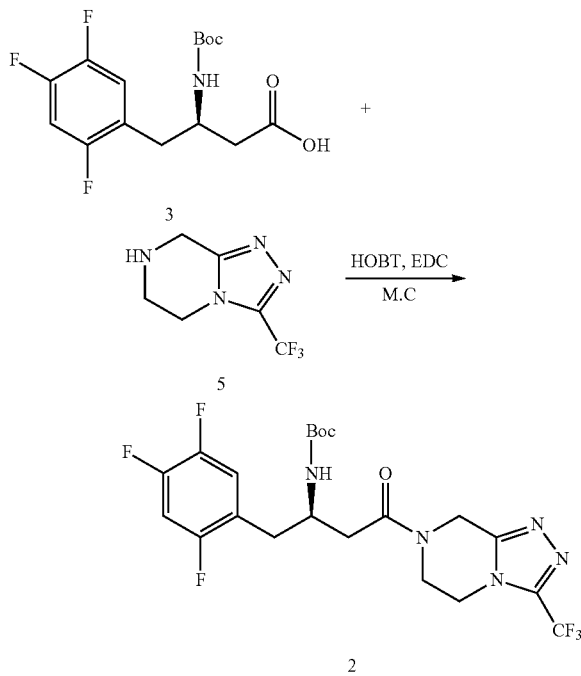

[Reaction Scheme 1]

However, the foregoing method of Reaction Scheme 1 disadvantageously employs expensive reaction reagents, 1-hydroxybenzotriazole (HOBT) and 1-ethyl-3-(3-dimethylaminopropyl)carbodiimide (EDC) and exhibits a very low product yield. Therefore, this method is not suitable for industrial-scale application.

DISCLOSURE OF INVENTION

Technical Problem

Therefore, the present invention is intended to provide a method for preparing a compound of formula 2 which is economical due to the use of inexpensive reagents and exhibits an excellent product yield and is therefore suitable for industrial-scale mass production.

Solution To Problem

The present invention provides a method for preparing a compound of formula 2. which includes reacting a compound of formula 3 with 3-(trifluoromethyl)-5,6,7,8-tetrahydro-[1,2,4]triazolo[4,3-α]pyrazine or a salt thereof in an organic solvent in the presence of 2-chloro-4,6-dimethoxy-1,3,5-triazine and a tertiary organic amine.

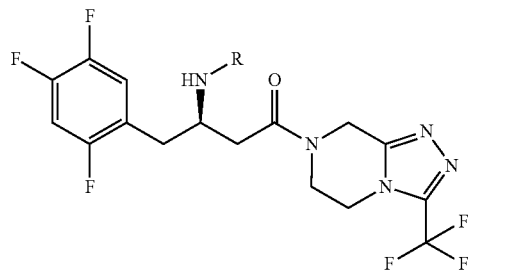

[Formula 2]

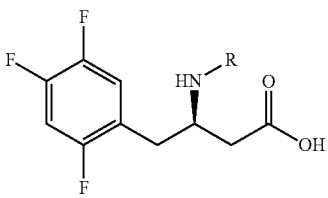

[Formula 3]

In the formulae 2 and 3, R is t-butyloxycarbonyl (Boc), benzyloxycarbonyl (Cbz), fluorenylmethyloxycarbonyl (Fmoc), acetyl or benzoyl.

In the present invention, R in formulae 2 and 3 is preferably Boc or Cbz.

In the present invention, the compound of formula 3 used as a starting material is commercially available or may be prepared by the method of INTERMEDIATE 3 disclosed in U.S. Pat. No. 6,699,871, Column 23. With regard to the compound of formula 3 of the present invention, when R is Cbz, Fmoc, acetyl or benzoyl, the corresponding compound may be prepared by using benzyl chloroformate, fluorenylmethyloxycarbonyl chloride, acetyl chloride or benzoyl chloride in place of di-tert-butyldicarbonate in Step B of the production method of INTERMEDIATE 3 disclosed in U.S. Pat. No. 6,699,871, Column 23.

In the present invention, 2-chloro-4,6-dimethoxy-1,3,5-triazine, which corresponds to a compound of formula 4 below, may be commercially available.

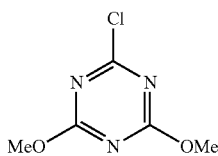

[Formula 4]

3-(trifluoromethyl)-5,6,7,8-tetrahydro-[1,2,4]triazolo[4,3-α]pyrazine, which corresponds to a compound of formula 5 below used as a reactant in the present invention, or a salt thereof is commercially available or may be prepared by the method disclosed in U.S. Pat. No. 6,699,871. The salt of the compound of formula 5 may be in the form of a hydrochloride, sulfate, phosphate, methanesulfonate or p-toluenesulfonate thereof.

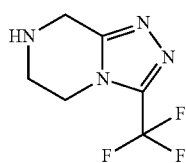

[Formula 5]

As used herein, the term "tertiary organic amine" refers to a base which is commonly used for the formation of an amide bond in the field of organic chemistry. Examples of the tertiary organic amine include N-methylmorpholine, pyridine, triethylamine, trimethylamine, triisopropylamine and quinoline.

The reaction molar ratio of the compound of formula 3:the compound of formula 5 in the present invention may vary but is preferably in the range of 1:0.8 to 3 and more preferably 1:1.1 to 1.3.

The reaction molar ratio of the compound of formula 3:the compound of formula 4 in the present invention may vary but is preferably in the range of 1:1 to 3 and more preferably 1:1.1 to 1.4.

The reaction molar ratio of the compound of formula 3:N-methylmorpholine in the present invention may vary but is preferably in the range of 1:2 to 5, more preferably 1:2.5 to 4.0 and most preferably 1:3.

The organic solvent used in the present invention may be a common organic solvent which is used for an amide-forming reaction in the field of organic chemistry. For example, the organic solvent is preferably selected from the group consisting of tetrahydrofuran, N,N-dimethylformamide, toluene and dichloromethane.

The preparation method of the present invention may be carried out at a wide range of temperatures which do not cause side reactions, but is carried out at a reaction temperature of about 0 to about 35° C. and preferably about 0 to 30° C. Specifically, starting materials, reactants and the like are mixed at a temperature of more preferably about 0 to about 10° C. and even more preferably about 0 to about 5° C., followed by warming to room temperature and reaction. As used herein, the term "room temperature" refers to a temperature of about 15 to 30° C.

The preparation method of the present invention may further include crystallizing the compound of formula 2 using at least one solvent selected from ethyl acetate, isopropyl alcohol, ethanol, methanol, dichloromethane, hexane, acetonitrile and tetrahydrofuran.

Crystallization may be carried out according to a method conventionally used by a person of ordinary skill in the art.

Further, the present invention provides a method for preparing a sitagliptin phosphate monohydrate, which includes the method for preparing a compound of formula 2 in accordance with the present invention.

Advantageous Effects Of Invention

The preparation method of the present invention enables the economical and high-yield production of a compound of formula 2 which is a key intermediate of sitagliptin and is therefore applicable to industrial-scale mass production.

MODE FOR THE INVENTION

Hereinafter, the present invention will be described in more detail with reference to the following examples. These examples are provided only for illustrating the present invention and should not be construed as limiting the scope and spirit of the present invention.

EXAMPLE 1

Preparation of tert-butyl (R)-4-(3-(trifluoromethyl)-5,6-dihydro-[1,2,4]triazolo[4,3-α]pyrazin-7(8H)-yl)1-1-(2,4,5-trifluorophenyl)-4-oxobutan-2-ylcarbamate (Compound of formula 2 wherein R is Boc)

(R)-3-Boc-amino-4-(2,4,5-trifluorophenyl)-butanoic acid (3.0 g, 9.0 mmol) and tetrahydrofuran (THF, 30 ml) were charged and dissolved in a dry flask, and N-methylmorpholine (2.97 ml, 27.0 mmol) was added thereto. Then, the mixture was cooled to a temperature of 0 to 5° C., and 2-chloro-4,6-dimethoxy-1,3,5-triazine (2.05 g, 11.7 mmol) was added thereto. After being stirred at a temperature of 0 to 5° C. for one hour, 3-(trifluoromethyl)-5,6,7,8-tetrahydro-[1,2,4]triazolo[4,3-α]pyrazine hydrochloride (2.47 g, 10.8 mmol) was added and the reaction mixture was stirred while elevating to a temperature of 20 to 25° C. After the completion of the reaction was confirmed by TLC, the reaction liquid was cooled to 10° C., and dichloromethane (30.0 ml) and water (30.0 ml) were added thereto, followed by separation of layers. The organic layer was washed with saturated sodium bicarbonate (30.0 ml) and saline (30.0 ml), dried over anhydrous sodium sulfate, concentrated under reduced pressure, and then crystallized from ethyl acetate (12.0 ml) and isopropyl alcohol (6.0 ml) to afford 4.29 g (yield: 94.0%) of tert-butyl (R)-4-(3-(trifluoromethyl)-5,6-dihydro-[1,2,4]triazolo[4,3-α]pyrazin-7(8H)-yl)-1-(2,4, 5-trifluorophenyl)-4-oxobutan-2-ylcarbamate.

1H NMR δ 7.04(dd, 1H, J=0.012), 6.84(dd, 1H, J=0.013), 5.01(s, 2H), 4.90(NH), 4.20(s, 2H), 4.10(t, 2H), 4.04(t, 2H), 3.97(m, 1H), 2.97(t, 2H), 2.70 (t, 2H), mp: 183.0 to 183.5° C. (as measured using a capillary melting point apparatus Mettler FP90 at an elevation rate of 2° C/min)

EXAMPLE 2

Preparation of benzyl (R)-4-(3-(trifluoromethyl)-5,6-dihydro-[1,2,4]triazolo[4,3-α]pyrazin-7(8H)-yl)-1-(2,4,5-trifluorophenyl)-4-oxobutan-2-ylcarbamate (Compound of formula 2 wherein R is Cbz)

(R)-3-Cbz-amino-4-(2,4,5-trifluorophenyl)-butanoic acid (3.0 g, 8.2 mmol) and tetrahydrofuran (THF, 30 ml) were charged and dissolved in a dry flask, and N-methylmorpholine (2.7 ml, 24.5mmol) was added thereto. Then, the mixture was cooled to a temperature of 0 to 5° C., and 2-chloro-4,6-dimethoxy-1,3,5-triazine (1.86 g, 10.6 mmol) was added thereto. After being stirred at a temperature of 0 to 5° C. for one hour, 3-(trifluoromethyl)-5,6,7,8-tetrahydro-[1,2,4]triazolo[4,3-α]pyrzine hydrochloride (2.05 g, 9.0 mmol) was added and the reaction mixture was stirred while warming to room temperature (20 to 25° C.). After the completion of the reaction was confirmed by TLC, the reaction liquid was cooled to 10° C., and dichloromethane (30.0 ml) and water (30.0 ml) were added thereto, followed by separation of layers. The organic layer was washed with saturated sodium bicarbonate (30.0 ml) and saline (30.0 ml), dried over anhydrous sodium sulfate, concentrated under reduced pressure, and then crystallized from ethyl acetate (12.0 ml) and isopropyl alcohol (6.0 ml) to afford 3.98 g (yield: 90%) of benzyl-(R)-4-(3-(trifluoromethyl)-5,6-dihydro-[1,2,4]-triazolo[4,3-α]pyrazin-7(8H)-yl)-1-(2,4, 5-trifluorophenyl)-4-oxobutan-2-ylcarbamate.

1H NMR δ7.10-7.34(m, 5H), 7.04(dd, 1H, J=0.012), 6.84 (dd, 1H, J=0.013), 5.01(s, 2H), 4.90(NH), 4.20(s, 2H), 4.10(t, 2H), 4.04(t, 2H), 3.97(m, 1H), 2.97(t, 2H), 2.70(t, 2H)

Comparative Example 1

Preparation of Compound of formula 2 wherein R is Boc, according to the method disclosed in U.S. Pat. No. 6,699,871. Example 7. STEP A (R)-3-Boc-amino-4-(2,4,5-trifluorophenyl)-butanoic acid (50.1 mg, 0.15 mmol) was dissolved in dichloromethane (2.5 ml) and 3-(trifluoromethyl)-5,6,7,8-tetrahydro-[1,2,4]triazolo[4,3-α]pyrazine (39.2 mg, 0.20 mmol) was added thereto. While maintaining a temperature of 0 to 5° C., HOBT (17.2 mg, 0.21 mmol) was added to the mixture, followed by reaction for 10 minutes. Thereafter, EDC (48.3 mg, 0.25 mmol) was added at 0° C., and the reaction mixture was warmed to room temperature and stirred for 14 hours. After the reaction was completed, the reaction liquid was concentrated under reduced pressure and a desired compound was purified by column chromatography eluting with 100% ethyl acetate to afford 29 mg (yield: 47.5%) of the title compound as a solid.

The invention claimed is:

1. A method for preparing a compound of Formula 2:

[Formula 2]

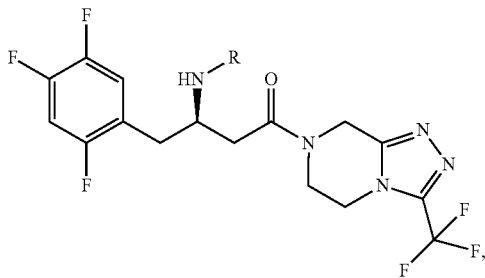

wherein R is t-butyloxycarbonyl (Boc), benzyloxycarbonyl (Cbz), fluorenylmethyloxycarbonyl (Fmoc), acetyl or benzoyl, comprising:

reacting a compound of Formula 3:

[Formula 3]

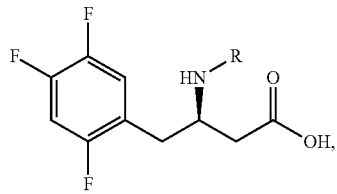

wherein R is t-butyloxycarbonyl (Boc), benzyloxycarbonyl (Cbz), fluorenylmethyloxycarbonyl (Fmoc), acetyl or benzoyl, with 3-(trifluoromethyl)-5,6,7,8-tetrahydro-[1,2,4]triazolo[4,3-α]pyrazine or a salt thereof in an organic solvent in the presence of 2-chloro-4,6-dimethoxy-1,3,5-triazine and a tertiary organic amine to produce a compound of Formula 2.

2. The method of claim 1, wherein R in Formula 2 and Formula 3 is Boc or Cbz.

3. The method of claim 1, wherein the tertiary organic amine is N-methylmorpholine, pyridine, triethylamine, trimethylamine, triisopropylamine or quinoline.

4. The method of claim 3, wherein the tertiary organic amine is N-methylmorpholine.

5. The of claim 1, wherein the organic solvent is selected from the group consisting of tetrahydrofuran, N,N-dimethylformamide, toluene and dichloromethane.

6. The method of claim 1, wherein the reaction is carried out at a temperature of 0 to 30° C.

7. The method of claim 1, further comprising adding ethyl acetate and isopropyl alcohol to form a crystallized compound of Formula 2.

8. The method of claim 2, further comprising adding ethyl acetate and isopropyl alcohol to form a crystallized compound of Formula 2.

9. The method of claim 3, further comprising adding ethyl acetate and isopropyl alcohol to form a crystallized compound of Formula 2.

10. The method of claim 4, further comprising adding ethyl acetate and isopropyl alcohol to form a crystallized compound of Formula 2.

11. The method of claim 5, further comprising adding ethyl acetate and isopropyl alcohol to form a crystallized compound of Formula 2.

12. The method of claim 6, further comprising adding ethyl acetate and isopropyl alcohol to form a crystallized compound of Formula 2.

13. A method for preparing a sitagliptin phosphate monohydrate, comprising:
preparing a compound of Formula 2 according to the method of claim 1; and
treating the compound of Formula 2 to yield sitagliptin phosphate monohydrate.

14. A method for preparing a sitagliptin phosphate monohydrate, comprising:
preparing a compound of Formula 2 according to the method of claim 2; and
treating the compound of Formula 2 to yield sitagliptin phosphate monohydrate.

15. A method for preparing a sitagliptin phosphate monohydrate, comprising:
preparing a compound of Formula 2 according to the method of claim 3; and treating the compound of Formula 2 to yield sitagliptin phosphate monohydrate.

16. A method for preparing a sitagliptin phosphate monohydrate, comprising:
    preparing a compound of Formula 2 according to the method of claim 4; and
    treating the compound of Formula 2 to yield sitagliptin phosphate monohydrate.

17. A method for preparing a sitagliptin phosphate monohydrate, comprising:
    preparing a compound of Formula 2 according to the method of claim 5; and
    treating the compound of Formula 2 to yield sitagliptin phosphate monohydrate.

18. A method for preparing a sitagliptin phosphate monohydrate, comprising:
    preparing a compound of Formula 2 according to the method of claim 6; and
    treating the compound of Formula 2 to yield sitagliptin phosphate monohydrate.

* * * * *

UNITED STATES PATENT AND TRADEMARK OFFICE
CERTIFICATE OF CORRECTION

PATENT NO. : 9,006,436 B2
APPLICATION NO. : 13/977919
DATED : April 14, 2015
INVENTOR(S) : Geun Gho Lim et al.

It is certified that error appears in the above-identified patent and that said Letters Patent is hereby corrected as shown below:

IN THE TITLE PAGES:

In Item (56) References Cited, in OTHER PUBLICATIONS, at page 1, column II, lines 5-9, please replace "ST Pharm. Website Product-Generic Intermediates, "Arabidopsis halleri subsp. halleri clone 99.4.1 ribosomal RNA intergenic region and external transcribed spacer region, completesequence," [online][retrieved on Aug. 12, 2013] Retrieved from:<URL:stpharm.co.kr/english/html/product/product12.asp>, 2 pages." with —ST Pharm Website, "Generic Products-Generic Intermediates." [online][retrieved on Aug. 12, 2013] Retrieved from:<URL:stpharm.co.kr/english/html/product/product12.asp>, 2 pages.—.

IN THE SPECIFICATION:

At column 4, lines 23-26, please replace "Preparation of tert-butyl (R)-4-(3-(trifluoromethyl)-5,6-dihydro-[1,2,4]triazolo[4,3-α]pyrazin-7(8H)-yl)1-1-(2,4,5-trifluorophenv1)-4-oxobutan-2-ylcarbamate" with —Preparation of tert-butyl (R)-4-(3-(trifluoromethyl)-5,6-dihydro-[1,2,4]triazolo[4,3-α]pyrazin-7(8H)-yl)-1-(2,4,5-trifluorophenyl)-4-oxobutan-2-ylcarbamate—; and Signed and Sealed this
First Day of September, 2015

Michelle K. Lee
*Director of the United States Patent and Trademark Office*

CERTIFICATE OF CORRECTION (continued)
U.S. Pat. No. 9,006,436 B2

At column 4, lines 59-63, please replace "Preparation of benzvl (R)-4-(3-(trifluoromethyl)-5,6-dihydro-[1,2,4]triazolo[4,3-α]pyrazin-7(8H)-yl)-l-(2,4,5-trifluorophenyl)-4-oxobutan-2-ylcarbamate" with —Preparation of benzyl (R)-4-(3-(trifluoromethyl)-5,6-dihydro-[1,2,4]triazolo[4,3-α]pyrazin-7(8H)-yl)-1-(2,4,5-trifluorophenyl)-4-oxobutan-2-ylcarbamate—.

IN THE CLAIMS:

Column 6, line 28 to line 30 should read

5. The method of claim 1, wherein the organic solvent is selected from the group consisting of tetrahydrofuran, N,N-dimethylformamide, toluene and dichloromethane.